Dec. 25, 1951 G. DE RUITER Plant Pat. 1,058
ROSE PLANT
Filed Aug. 15, 1950
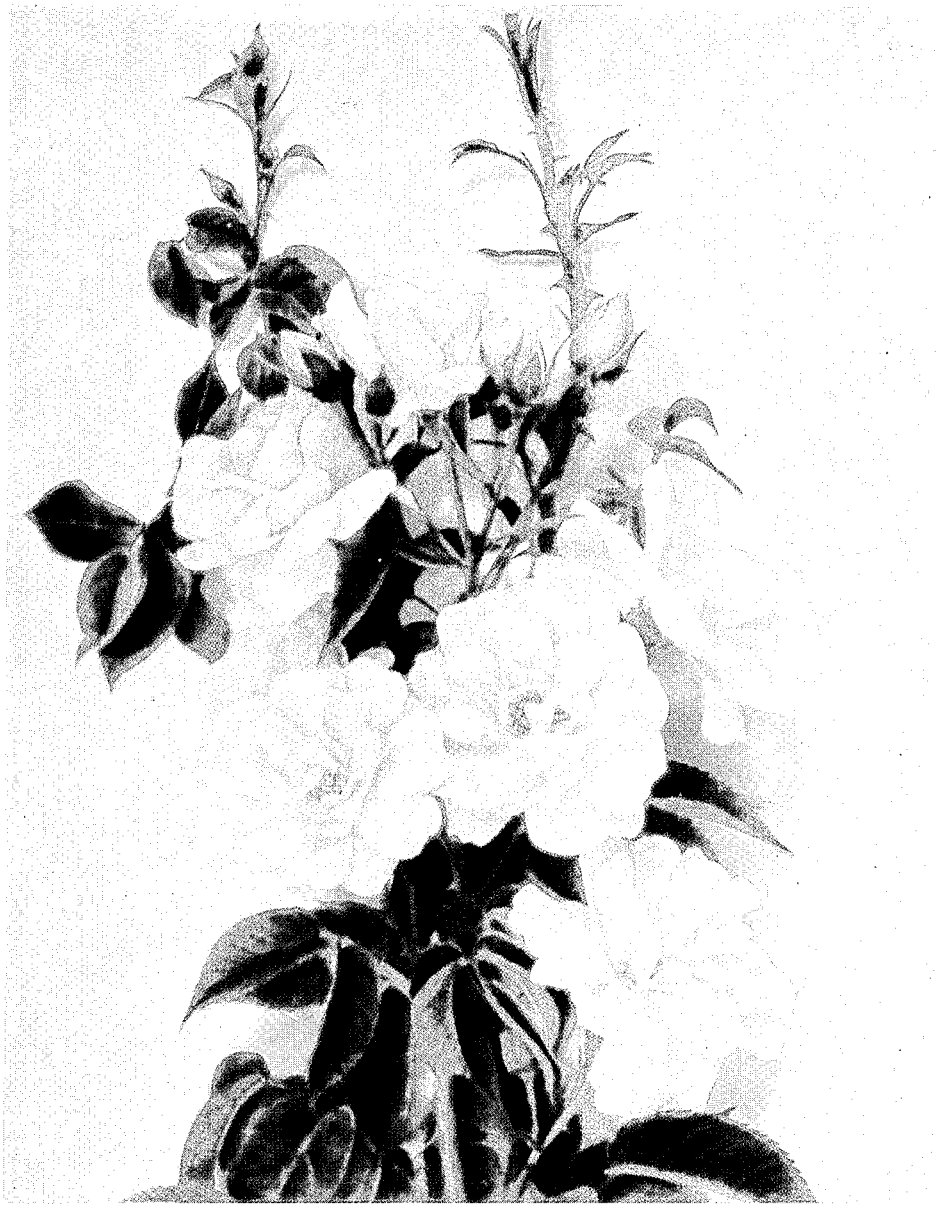
Inventor.
Gerrit de Ruiter
By: Robert Cobb
Attorneys.

Patented Dec. 25, 1951

Plant Pat. 1,058

UNITED STATES PATENT OFFICE 1,058

ROSE PLANT

Gerrit De Ruiter, Hazerswoude, Netherlands, assignor to Jackson & Perkins Company, Newark, N. Y., a corporation of New York Application August 15, 1950, Serial No. 179,615

1 Claim. (Cl. 47—61)

The present invention relates to a new and distinct variety of rose plant of the so-called Park type, originating by crossing the variety "Sangerhausen" (unpatented) with an unnamed seedling.

As a result of this cross, I have produced a rose which is distinctive from the type known as floribundas, as well as from the type known as hybrid teas, and which is of the type commonly known as a Park rose. In reality, this new variety is a marked improvement over the old-fashioned pink variety "F. J. Grootendorst" (unpatented), which has so commonly been used in shrub borders, etc.

This new variety is distinguished from its parents and from other rose varieties by the large size and type of individual florets forming large clusters on the ends of long stems, which attain a length of from four to five feet; by the Thulite Pink shaded with Eosine Pink color of the flowers; by its recurrent habit, generous production of wood and bloom; and by its disease resistance.

Asexual reproduction of this new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature:

Parentage: Seedling.

*Seed parent.*—"Sangerhausen."

*Pollen parent.*—Unnamed seedling.

Classification: Botanic and commercial — tall polyantha.

*Flower*

(Observations made outdoors in the fields at Newark, New York, in the early afternoon, late in the month of September 1949.)

Blooming habit: Recurrent—continuous.

Bud:

*Size.*—Medium.

*Form.*—Ovoid. Is not affected by wet or hot weather.

*Color.*—When sepals first divide—Rose Color, Plate 12. When petals begin to unfurl—Eosine Pink, Plate 1. When half blown—inside of petals: Eosine Pink, Plate 1, overcast with Rose Pink, Plate 12; reverse of petals: Thulite Pink, Plate 26, overcast with Rose Pink, Plate 12.

*Sepals.*—Slightly branched; curl back when petals begin to unfurl. Color—inside—Light Green, Plate 31; reverse — Jade Green, Plate 31.

*Calyx.* — Shape — pear. Size—small. Aspect—smooth. Odor when rubbed—none. Color—Light Hellebore Green, Plate 17.

*Peduncle.*—Length—short. Aspect — rough. Color—Bice Green, Plate 17. Strength—erect; slender.

*Opening.*—Bud opens up well. Is not affected by adverse weather conditions.

Bloom:

*Size.*—Medium. Average size when fully expanded—2½ inches.

*Borne.*—In flat clusters.

*Stems.*—Medium length; strong.

*Form.*—When first open—cupped. Permanence—flattens.

*Petalage.*—Double (full but open center). Number of petals under normal conditions, 25 to 30.

*Color.*—Center of flower—Thulite Pink, Plate 26, shaded with Eosine Pink, Plate 1. Outer petals—La France Pink, Plate 1, lightly overcast with Rose Pink, Plate 12. Base of petals (aiglet) — Marguerite Yellow, Plate 30. Inside of petals—Thulite Pink, Plate 26, overcast with La France Pink, Plate 1. Reverse of petals—Rose Pink, Plate 12, overcast with Hermosa Pink, Plate 1. General tonality from a distance—Thulite Pink, Plate 26, overcast with La France Pink, Plate 1.

*Discoloration.*—General tonality at end of first day—Thulite Pink, Plate 26, lightly overcast with Eosine Pink, Plate 1. Second day—Thulite Pink, Plate 26, lightly overcast with Hermosa Pink, Plate 1. Third day—La France Pink, Plate 1, lightly overcast with Rose Pink, Plate 12.

Petals:

*Texture.*—Thin. Is not affected by wet or hot weather.

*Appearance.* — Inside — shiny. Outside — satiny.

*Form.*—Oval.

*Arrangement.*—Informal (with "rags" in center). Petaloids in center—few; small.

*Persistence.*—Drop off cleanly.

*Fragrance.*—Slight. Nature—fruity (Russet apple).

*Lasting quality.*—On the plant—long.

Genital Organs:

*Stamens, anthers.*—Size—medium. Color—Apricot Yellow, Plate 4. Arrangement—regular around styles.

*Stamens, filaments (threads).*—Length—medium. Color—Baryta Yellow, Plate 4.

*Pollen.*—Color—Maize Yellow, Plate 4.

*Styles.*—Bunched, uneven length; medium length; thin.

*Stigmas.*—Color—Pale Green Yellow, Plate 5.

*Ovaries.*—All enclosed in calyx.

*Plant*

Form: Bush.

Growth: Vigorous; upright; about 4 to 5 foot stems with repeating clusters of blooms on the end of the stem.

Foliage: 5 to 7 leaflets.

*Size.*—Medium.

*Quantity.*—Normal

*Color.*—New foliage—upper side—Yellowish Oil Green, Plate 5, lightly overcast with Oxblood Red, Plate 1, and serrations Oxblood Red, Plate 1; under side—Yellowish Oil Green, Plate 5, overcast with Oxblood Red, Plate 1. Old foliage—upper side—Cress Green, Plate 31; under side—Jade Green, Plate 31.

*Shape.*—Oval pointed.

*Texture.* — Upper side — leathery. Under side—smooth. Ribs and veins—ordinary.

*Edge.*—Serrated (saw toothed).

*Serration.*—Single; small.

*Leaf stem.*—Color—Light Elm Green, Plate 17. Under side—rough.

*Stipules.*—Medium length; bearded.

*Disease resistance.*—Resistant.

Wood:

*New wood.* — Color — Oil Green, Plate 5. Bark—smooth.

*Old wood.*—Color—Light Elm Green, Plate 17. Bark—smooth.

Thorns:

*Thorns.* — Quantity — on main stalks from base and on laterals from stalk—ordinary. Form—flat base; medium length; hooked downward. Color when young—Oxblood Red, Plate 1. Position—irregular.

*Prickles and short needles.*—None.

I claim:

A new and distinct variety of rose plant of the Park type, characterized as to novelty by the large size and type of its individual florets forming large clusters borne on long stems, by the Thulite Pink shaded with Eosine Pink color of its blooms, by its generous production of wood and bloom, by its disease resistance, and by its recurrent habit, substantially as shown and described.

GERRIT DE RUITER.

No references cited.